United States Patent
Roorda et al.

(10) Patent No.: US 8,753,357 B2
(45) Date of Patent: Jun. 17, 2014

(54) DEVICES AND METHODS FOR SUTURING TISSUE

(75) Inventors: Wouter E. Roorda, Palo Alto, CA (US); Laveille K. Voss, Belmont, CA (US); David J. Milazzo, Santa Clara, CA (US); Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 399 days.

(21) Appl. No.: 13/111,416

(22) Filed: May 19, 2011

(65) Prior Publication Data
US 2012/0296347 A1    Nov. 22, 2012

(51) Int. Cl.
*A61B 17/04*    (2006.01)
*A61B 17/12*    (2006.01)

(52) U.S. Cl.
USPC .................................................. 606/144

(58) Field of Classification Search
USPC .............................. 606/139, 144–150
See application file for complete search history.

(56) References Cited

U.S. PATENT DOCUMENTS

| | | | | |
|---|---|---|---|---|
| 5,320,632 A * | 6/1994 | Heidmueller | ............... | 606/144 |
| 6,036,699 A * | 3/2000 | Andreas et al. | ............... | 606/139 |
| 6,743,241 B2 * | 6/2004 | Kerr | ............... | 606/144 |
| 6,939,357 B2 * | 9/2005 | Navarro et al. | ............... | 606/145 |
| 8,034,060 B2 * | 10/2011 | Keren et al. | ............... | 606/144 |
| 8,361,086 B2 * | 1/2013 | Allen et al. | ............... | 606/139 |

OTHER PUBLICATIONS

Grossman, W., Cardiac Catheterization and Angiography, 3rd Ed., Lea & Febiger, Philadelphia, pp. 1-49, 52-247. 1986.

\* cited by examiner

*Primary Examiner* — Melanie Tyson
(74) *Attorney, Agent, or Firm* — Workman Nydegger; Randy Shen

(57) ABSTRACT

A suture applying device includes a shaft which carries a pair of needles near its distal end. The needles are joined by a length of suture, and the shaft is used to both introduce the needles into a lumen of a body structure and to draw the needles back through tissue on either side of the puncture site. After the needles have passed through the tissue, they are captured by a needle receiver and drawn outward through the tract, leaving a loop of suture behind to close the puncture site near the body lumen. The suture can then be tied or otherwise secured to close the puncture site.

24 Claims, 11 Drawing Sheets

DEVICES AND METHODS FOR SUTURING TISSUE

FIELD OF THE INVENTION

The present invention relates generally to devices and methods for the percutaneous closure of body lumens. More particularly, the present invention relates to devices and methods for the percutaneous closure of arterial and venous puncture sites, which are usually accessible only through a tissue tract.

BACKGROUND OF THE INVENTION

A number of diagnostic and interventional vascular procedures are now performed transluminally, where a catheter is introduced to the vascular system at a convenient access location and guided through the vascular system to a target location using established techniques. Such procedures require vascular access which is usually established using the well known Seldinger technique, as described, for example, in William Grossman's "Cardiac Catheterization and Angiography," 3rd Ed., Lea and Febiger, Philadelphia, 1986, which is incorporated herein by reference in its entirety.

When vascular access is no longer required, the introducer sheath must be removed and bleeding at the puncture site stopped. One common approach to providing hemostasis (the cessation of bleeding) is to apply external force near and upstream from the puncture site, typically by manual or "digital" compression. This approach suffers from a number of disadvantages. It is time-consuming, frequently requiring one-half hour or more of compression before hemostasis is assured. This procedure is uncomfortable for the patient and frequently requires administering analgesics to be tolerable. Moreover, the application of excessive pressure can at times totally occlude the underlying blood vessel, resulting in ischemia and/or thrombosis. Following manual compression, the patient is required to remain recumbent for at least six and at times as long as eighteen hours under close observation to assure continued hemostasis. During this time, renewed bleeding may occur resulting in bleeding through the tract, hematoma and/or pseudoaneurism formation as well as arteriovenous fistula formation. These complications may require blood transfusions and/or surgical intervention. The incidence of these complications increases when the sheath size is increased and when the patient is anti-coagulated. It is clear that the standard technique for arterial closure can be risky, and is expensive and onerous to the patient. While the risk of such conditions can be reduced by using highly trained individuals, such use is both expensive and inefficient.

To overcome the complications associated with manual compression, the use of bioabsorbable fasteners to stop bleeding has been proposed by several groups. Generally, these approaches rely on the placement of a thrombogenic and bioabsorbable material, such as collagen, at the superficial arterial wall over the puncture site. While potentially effective, this approach suffers from a number of shortcomings. It can be difficult to properly locate the interface of the overlying tissue and the adventitial surface of the blood vessel, and locating the fastener too far from that surface can result in failure to provide hemostasis and subsequent hematoma and/or pseudo aneurism formation. Conversely, if the fastener intrudes into the arterial lumen, intravascular clots and/or collagen pieces with thrombus attached can form and embolize downstream causing vascular occlusion. Also, thrombus formation on the surface of a fastener protruding into the lumen can cause a stenosis which can obstruct normal blood flow. Other possible complications include infection as well as adverse reactions to the collagen implant.

For these reasons, it would be desirable to provide improved devices and methods to seal body lumen puncture sites. It would be particularly desirable to provide percutaneous devices and methods for suturing the puncture sites required for percutaneous vascular procedures.

SUMMARY OF THE INVENTION

The present invention provides devices and methods for suturing percutaneous lumenal puncture sites. The devices may comprise a shaft, at least one pair of needles removably carried near the distal end of the shaft, and a length of suture secured to and extending between each pair of needles. As described below, the shaft is used to introduce the needles inwardly through the tract and puncture site and into the lumen. Thereafter, the shaft is used to draw the needles outwardly back through the tissue on either side of the puncture site to begin forming one or more suture loops at the intimal surface of the puncture site. The device may further include means for capturing the pointed ends of the needles after they have passed through the tissue and back into the tract. The means for capturing the needles and/or the shaft can then be withdrawn to carry the needles and attached suture outwardly back through the tract. The free ends of the suture(s) can then be tied (or otherwise secured) and the resulting knot pushed back through the tract to complete the suture loop(s) at the adventitial surface of the puncture site. The ability to provide a secured suture loop at the puncture site is particularly advantageous since a reliable closure is formed. Furthermore, suture closure of puncture sites has been universally accepted as the standard of care for many decades.

The devices and methods of the present invention are useful whenever it is desirable to place a tied or otherwise secured suture loop to close a lumen puncture site, and will be particularly useful for suturing percutaneous vascular puncture sites. The devices can achieve closure wholly through the tract puncture site and can be manipulated entirely or substantially in a percutaneous manner. The present invention may be particularly useful in the sealing of femoral artery cannulation sites made in connection with percutaneous transluminal procedures, such as angiography, angioplasty, atherectomy, laser ablation, stent placement, intravascular imaging, and the like. The present invention will also find use in other medical procedures which rely on percutaneous access to hollow body organs and lumens, such as laparoscopic procedures, endoscopic procedures, artheroscopic procedures, and the like.

Accordingly, in one exemplary embodiment, a suturing device may include a shaft having a proximal end and a distal end, a pair of needles, a length of suture secured to and extending between the needles, a needle receiver, and a barrel. The pair of needles may be removably carried near the distal end of the shaft. Each needle includes a first end and a second end having a sharpened tip. The needles are carried with the sharpened tips disposed toward the proximal end of the shaft and are selectively movable between a first position and a second position. The needle receiver may include a lumen that receives the shaft in sliding engagement, a distal end, and a pair of needle capture features formed in the distal end which receive and securely hold the needles after the shaft has been drawn proximally relative to the needle receiver. The barrel includes a proximal end and a distal end and is mounted on the shaft such that the shaft can slide relative to the barrel. The distal end of the barrel includes an aperture through which the shaft can extend and a pair of needle guides that are radially offset from one another. The needle guides are adapted to guide the needles into the needle capture features in a desired position.

In another exemplary embodiment, a suturing device includes a shaft having a proximal end and a distal end, a pair of needles, a length of suture secured to and extending between the needles, a barrel, and a needle receiver. The pair of needles are removably carried near the distal end of the shaft and each needle includes a shank carried near the distal end of the shaft and a sharpened tip disposed toward the proximal end of the shaft. Each needle is selectively movable between a first position that is generally parallel to the shaft and a second position that is angled relative to the shaft. The barrel has a proximal end and a distal end and is slidably mounted on the shaft to facilitate relative movement therebetween. The distal end of the barrel includes a pair of needle guides that guide the needles into the barrel in a predetermined orientation as the shaft is drawn proximally relative to the barrel. The needle receiver is slidably mounted on the shaft and at least partially within the barrel. The needle receiver is movable relative to the shaft and the barrel. The needle receiver includes a needle capture disc that extends radially away from the shaft and includes a pair of needle capture features which receive and securely hold the needles after the shaft has been drawn proximally to draw the needles through the needle guides and upon distal movement of the needle receiver.

A suturing device according to another exemplary embodiment includes a shaft having a proximal end and a distal end, a pair of needles, a length of suture secured to and extending between the needles, and a barrel. The pair of needles are removably carried near the distal end of the shaft and each needle includes a first end and a second end having a sharpened tip. The needles are carried with the sharpened tips disposed toward the proximal end of the shaft. The needles are selectively movable between a first position that is generally parallel to the shaft and a second position that is angled relative to the shaft. The barrel has a proximal end and a distal end and is slidably mounted on the shaft to facilitate relative movement therebetween. The distal end of the barrel includes a pair of needle guides and a pair of needle capture features. The needle guides are generally funnel-shaped to guide the needles toward the needle capture features as the shaft is drawn proximally relative to the barrel. The needle capture features are adapted to securely hold the needles after the shaft has been drawn proximally.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1:
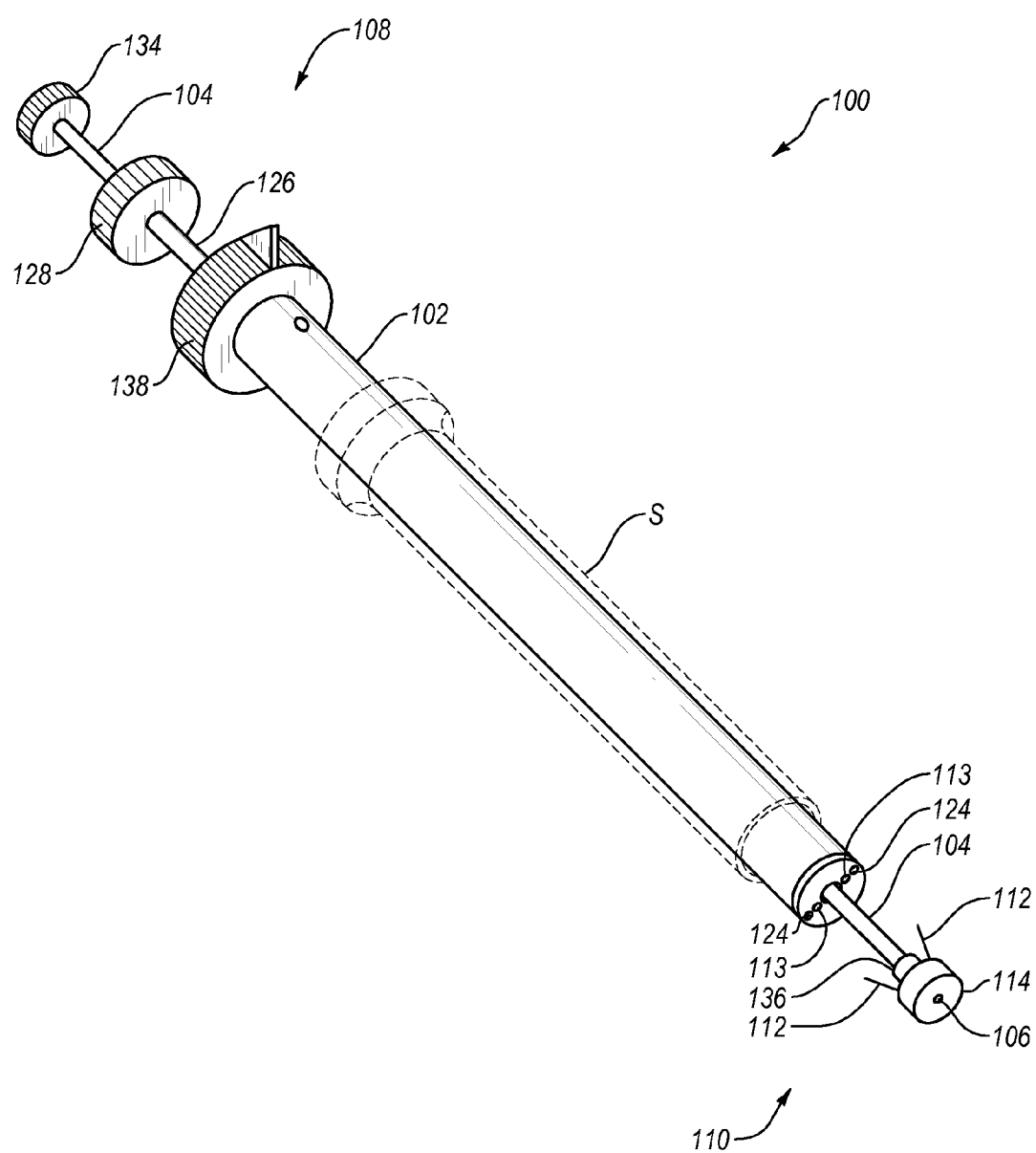
FIG. 1 is a perspective view of a suturing device according to one exemplary embodiment of the present invention.

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

The term "suturing" is herein intended to include the process of joining two surfaces or edges together with a fastener or so as to close an aperture, opening, or wound, or join tissues. The fastener is usually a suture such as a thread of material (either polymeric or natural), gut, wire, or the like. The term fastener as used herein also includes clamps, studs, hasps, catches, hooks, rivets, staples, snaps, stitches, VEL-CROC, buttons, and other coupling members.

Referring to FIGS. 1-7, a suture applying device 100 which is suitable for suturing and sealing of percutaneous vascular puncture sites, such as those made to the femoral artery in a patient's groin, will be described. It will be appreciated, however, that the device of the present invention can be readily adapted for use with punctures made to other hollow body organs and lumens, although it may be necessary to modify the dimensions and other particular aspects of the device to accommodate the different usage environments.

Device 100 of the present invention comprises an elongate body which includes an outer barrel 102 and inner shaft 104. Shaft 104 is slidably positioned within the barrel 102. Shaft 104 is hollow, defining a guidewire lumen 106 extending from the proximal end 108 to the distal end 110 of device 100. In this way, device 100 can be introduced over a conventional guidewire GW to facilitate introduction and manipulation of device 100 throughout the procedure, as described in detail hereinafter.

Suture applying device 100 will be introduced through a conventional introducer sheath S, shown in phantom in FIG. 1. The ability to introduce device 100 over guidewire GW is not essential to the present invention, but will generally be preferred since most physicians desire that intravascular devices be manipulated over a guidewire. Introduction through the introducer sheath S optionally provides containment of the sutures as they are being introduced, as discussed hereinafter.

Suture needles 112 are carried in a needle carrier 114 which is mounted on the distal end of shaft 104. The illustrated embodiment includes a single pair of suture needles 112, which are disposed on opposing sides of needle carrier 114. It will be appreciated, however, that device 100 may include additional pairs of suture needles 112 as needed or desired for a particular procedure. It will also be appreciated that needles 112 may also be positioned on needle carrier 114 in other arrangements that are not on opposing sides of needle carrier 114. Rather, needles 112 may be arranged on needle carrier 114 in any substantially any configuration so that they are radially offset from one another.

Figure 2A:
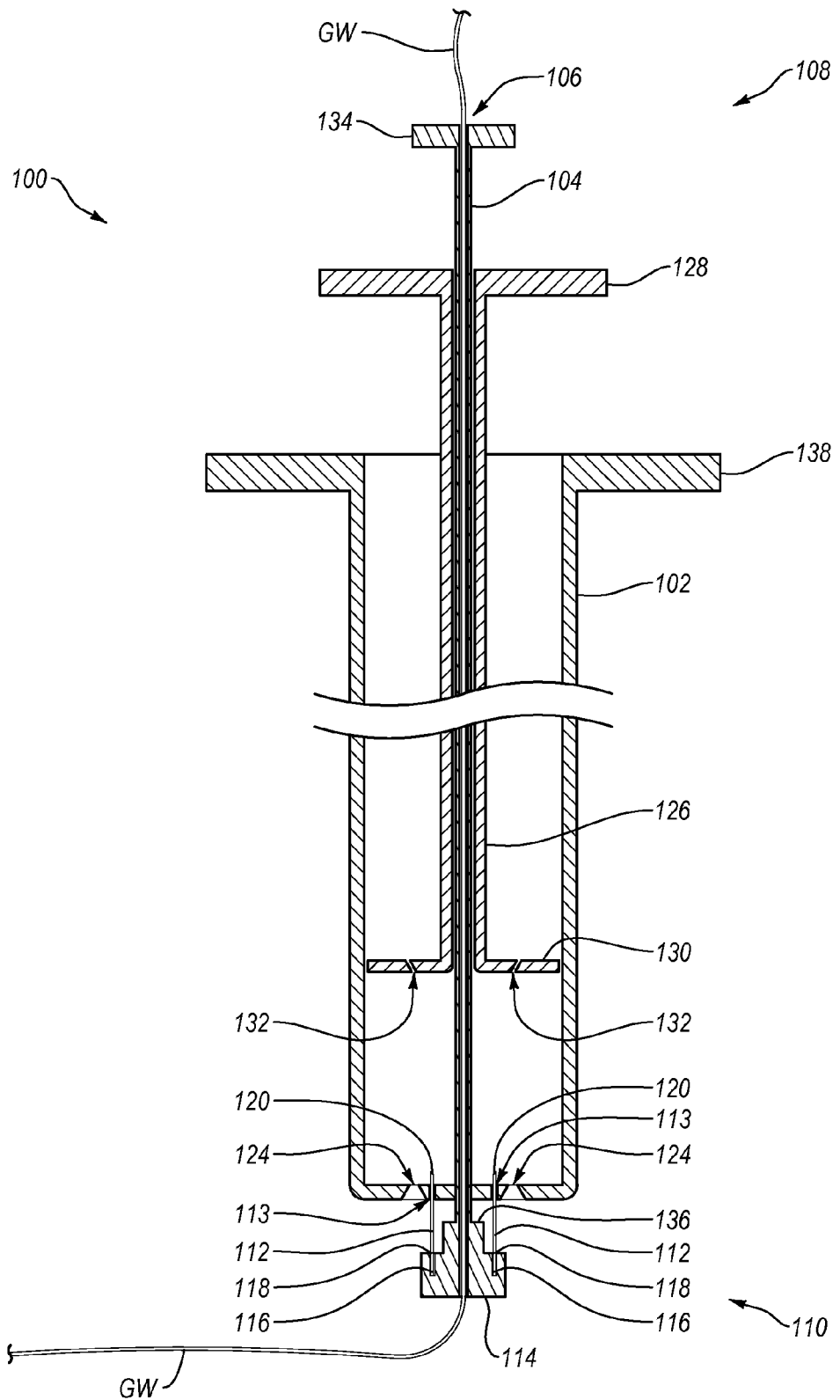
FIG. 2A is a cross-sectional view of the suturing device of FIG. 1, shown with the needles retracted for delivery into a vessel.
Figure 2B:
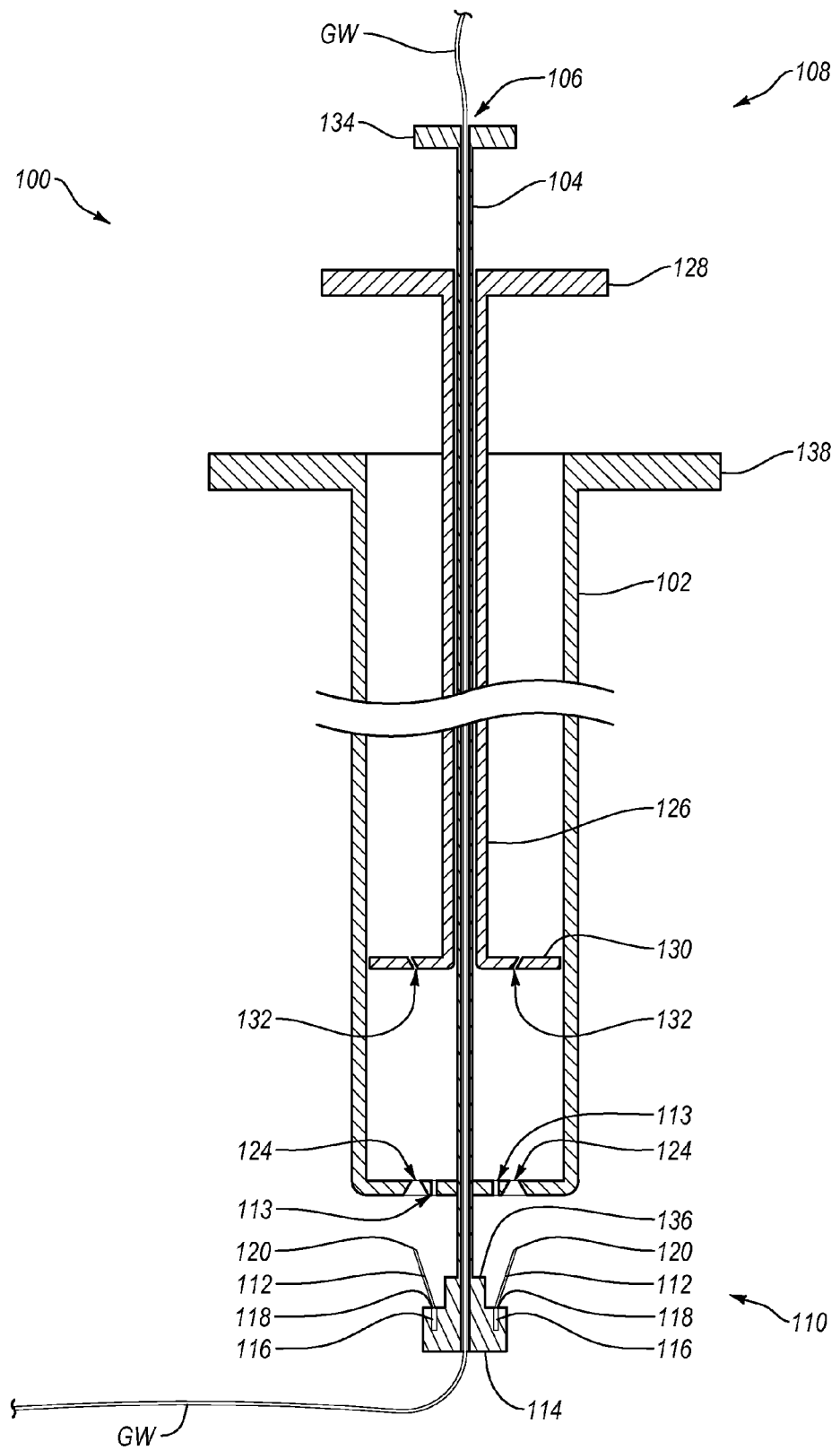
FIG. 2B is a cross-sectional view of the suturing device of FIG. 1, shown with the needles expanded.

Needle carrier 114 includes a pair of needle receptacles 116 that receive a distal shank portion 118 of each needle 112. Needle receptacles 116 are designed to hold needles 112 when needles 112 are in a first or introduction position or orientation, as shown in FIGS. 1 and 2A, while distal end 110 is introduced into a patient. In the first or introduction position, according to the presently illustrated embodiment, needles 112 are oriented generally parallel to shaft 104. Needle receptacles 116 are also designed to hold needles 112 when needles 112 are in a second or deployment position or orientation, as shown in FIG. 2B. In the second or deployment position, according to the presently illustrated embodiment, needles 112 are angled outwardly relative to shaft 104. That is, in the second or deployment position, the proximal ends 120 (i.e., the sharpened tips) of needles 112 are disposed radially further away from shaft 104 or the center of needle carrier 114 than distal shank portions 118 of needles 112.

Figure 3:
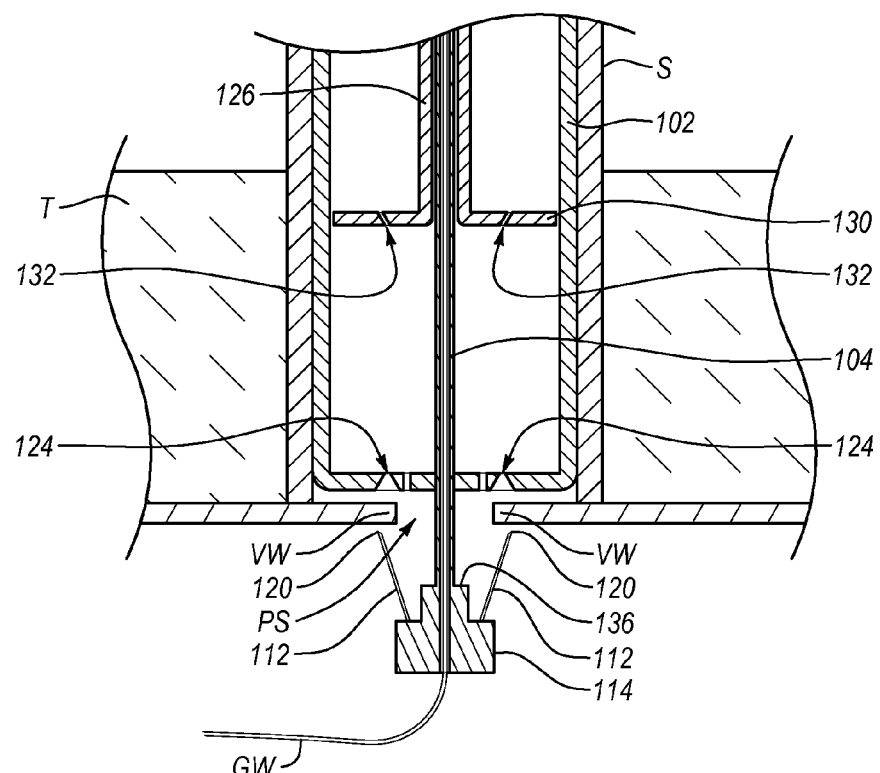
FIG. 3 is a detail cross-sectional view of the distal end of the suturing device of FIGS. 1 and 2, shown with the needles expanded for delivery through the vessel wall.

As discussed in greater detail below, needles 112 move or expand to the second or deployment position, as shown in FIGS. 2B and 3, once distal end 110 is properly positioned within the patient (e.g., once needle carrier 114 and needles 112 are positioned within the target vessel). As also described in greater detail hereinafter, this second or deployment position is desirable since it helps direct needles 112 through the vessel wall surrounding the puncture site, where needles 112 can be captured by a needle capturing assembly which is described hereinafter.

The movement or expansion of needles 112 could, of course, be achieved in a variety of ways. For instance, needles 112 may be biased toward the second, deployment position or orientation, but may be selectively retained in the first, introduction position or orientation. More specifically, as shown in FIGS. 1 and 2B, needles 112 may be held by needle carrier 114 so that proximal ends 120 are naturally angled away from shaft 104. Nevertheless, needle 112 may be flexed toward shaft 104 so as to be generally parallel with shaft 104 (e.g., in the first, introduction position or orientation). When needles 112 are oriented generally parallel to shaft 104, proximal ends 120 can be inserted into apertures 113 in the distal end of barrel 102 by drawing needle carrier 114 proximally. Positioning proximal ends 120 within apertures 113 maintains needles 112 in the first, introduction position until needles 112 are removed from apertures 113.

When it is desirable to move needles 112 to the second, deployment position (e.g., when needle carrier 114 is positioned at least partially within a vessel), needle carrier 114 may be moved distally. Distal movement of needle carrier 114 causes proximal ends 120 of needles 112 to exit apertures 113. When proximal ends 120 exit apertures 113, needles 112 return to their natural position or orientation (e.g., the second, deployment position or orientation), as shown in FIGS. 1 and 2B.

It will be appreciated that other means or mechanical mechanisms may be used to move or reorient needles 112 between the introduction and deployment positions. For instance, needles 112 may naturally be in the introduction position or orientation without having to be held in apertures 113. The movement or expansion of needles 112 from the first, introduction position to the second, deployment position may be accomplished with an effector (not shown) disposed about shaft 104. The effector may be linked to an actuator handle at proximal end 108 that facilitates the movement of the effector along a portion of the length of shaft 104. As the effector is moved distally, the distal end of the effector may engage needle carrier 114 in such a way that the distal end of the effector is directed radially. The distal end of the effector may engage needles 112 as the distal end of the effector is directed radially, thereby causing needles 112 to be moved or reoriented to the deployment position or orientation.

One of ordinary skill in the art will recognize still other mechanisms that may be used to move needles 112 between the introduction and deployment configurations. For instance, as discussed in greater detail below, FIGS. 13A-14B illustrate other exemplary manners in which needles may be moved or reoriented between introduction and deployment configurations.

Needles 112 are joined to one another by a length of suture 122 which is secured to each needle 112 and extends therebetween. Suture 122 may be stored on device 100 so that it is readily left behind in the body lumen as device 100 is withdrawn through the percutaneous penetration, as described in greater detail hereinafter. For instance, needle carrier 114 may include a suture receptacle that holds suture 122 until the needles are deployed. Suture 122 may be withdrawn from the suture receptacle when needles 112 are deployed and drawn through the vessel wall as described below. The suture receptacle may have an opening on the proximal side of needle carrier 114 so that suture 122 is withdrawn from the suture receptacle and freed from needle carrier 114 when needles 112 are drawn through the vessel wall.

Suture 122 may also be stored in other manners. For instance, suture 122 may simply be coiled around needle carrier 114. When needles 112 are removed from needle carrier 114, suture 122 may uncoil off of needle carrier 114. Alternatively, at least a portion of suture 122 may be stored within the distal end of barrel 102. The ends of suture 122 may extend out of barrel 102 and to distal shank portions 118 of needles 112 through an opening in barrel 102. For instance, suture 122 may extend out of barrel 102 through the same opening as shaft 104, through apertures 113, through needle guides 124, or through another opening in barrel 102. Still another option for storing suture 122 may include a distal sheath (not shown) extending from needle carrier 114. The distal sheath may be flexible enough to be passed through a puncture site and into a body lumen. The distal sheath may include an interior space for receiving suture 122 therein. Similar to barrel 102, the distal sheath may have an opening through which suture 122 may be withdrawn from the distal sheath.

Figure 9:
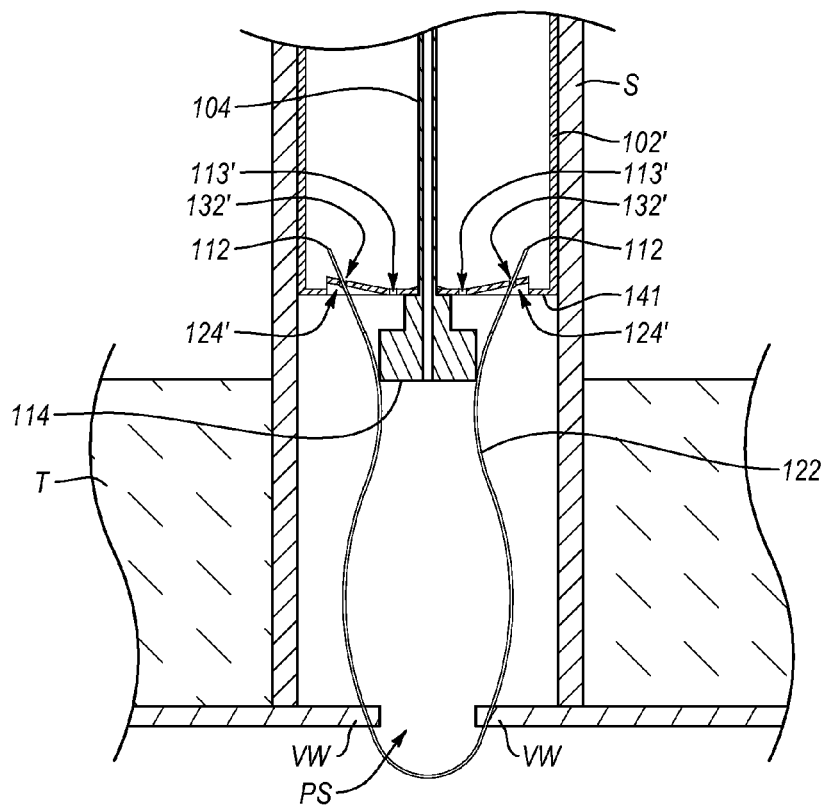
FIG. 9 illustrates a partial cross-sectional view of a suturing device according to another exemplary embodiment of the present invention, showing the needles and suture being drawn up through the vessel wall.
Figure 10:
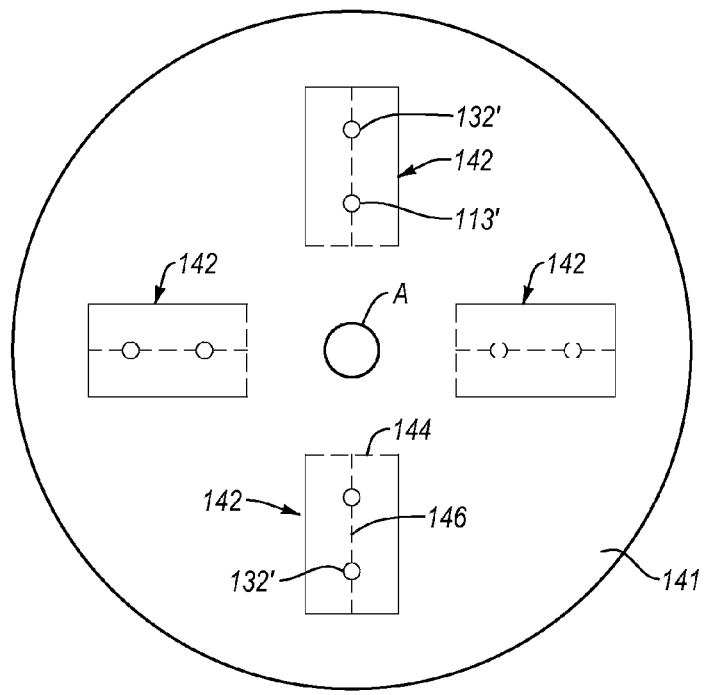
FIG. 10 illustrates a plan view of a needle receiver of the suturing device of FIG. 9.
Figure 11:
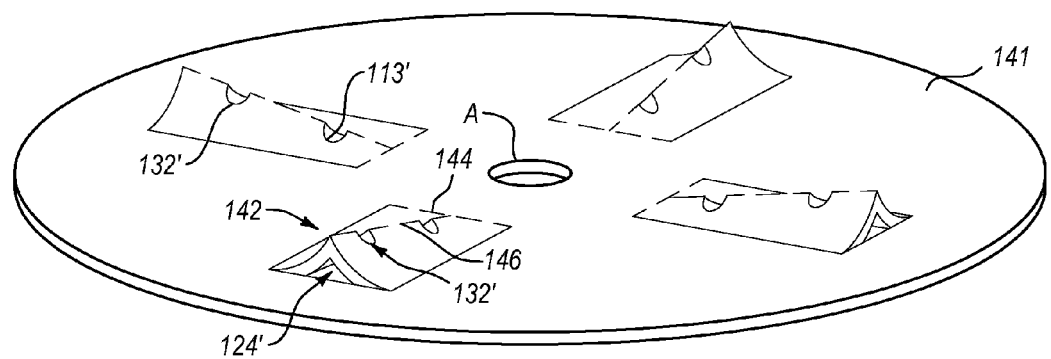
FIG. 11 illustrates a perspective view of the needle catch tabs of the needle receiver of FIGS. 9 and 10.

As noted above, device 100 also includes a needle capturing assembly for capturing needles 112 after they have been drawn at least partially through the vessel wall on either side of the puncture site. The needle capture assembly may take a variety of forms. The embodiment illustrated in FIGS. 1-7, for example, shows one possible needle capture assembly of the present invention. Nevertheless, other needle capture assemblies or mechanisms may be employed without departing from the scope of the present invention. For instance, FIGS. 9-11 illustrate another exemplary embodiment of a needle capture system according to the present invention.

Returning attention to FIGS. 1-7, the illustrated needle capture assembly includes a needle guide 124 for each needle 112. Needle guides 124 are funnel-shaped openings in the distal end of barrel 102. Each needle guide 124 is shaped, sized, and positioned so as to receive a needle 112 therethrough when needles 112 are drawn through the vessel wall.

Needle guides 124, and particularly the funnel-shape of needle guides 124, perform at least two main functions. First, needle guides 124 receive needles 112 therethrough so that needles 112 can be captured and drawn proximally by a needle receiver 126. Second, needle guides 124 ensure that needles 124 are properly oriented so as to be captured by needle receiver 126. When needles 112 are drawn through the vessel wall, calcified plaque may cause some deflection of needles 112. Nevertheless, the funnel-shape of needle guides 124 allows for needles 112 to be deflected while still enabling needle guides 124 to receive and direct needles 112 to the proper orientation for capture by needle receiver 126. More specifically, each needle guide 124 is designed with a relatively wide receiving area that receives a needle 112 even if needle 112 has been deflected while passing through the vessel wall. Needle guides 124 then taper to redirect or reorient needles 112 to a desired orientation as needles 112 continue to be drawn proximally.

As can be seen in FIG. 1, needle guides 124 are disposed radially further away from shaft 104 than apertures 113. As a result, when needles 112 exit apertures 113 and move to the deployment position (e.g., proximal ends 120 are angled away from shaft 104), proximal ends 120 are aligned with needle guides 124. Thus, once needles 112 are removed from apertures 113 and moved to the deployment position, needles 112 may be moved proximally so that proximal ends 120 are received by needle guides 124.

Although FIG. 1 illustrates apertures 113 and needle guides 124 as being aligned with one another, apertures 113 and needle guides 124 may be offset from one another. For instance, apertures 113 may be angularly offset from needle guides 124. In such a case, once needles 112 are removed from apertures 113, needle carrier 114 could be turned (by rotating handle 134) to align needles 112 with needle guides 124.

The needle capture assembly of the present embodiment also includes needle receiver 126. In the presently illustrated embodiment, needle receiver 126 is a plunger that is slidably mounted on shaft 104. Needle receiver 126 has a handle 128 at a proximal end thereof and a needle capture disc 130 at a distal end thereof. Needle capture disc 130 is disposed at least partially within barrel 102. Handle 128 can be used to move needle capture disc 130 at least partially along the length of shaft 104. When moved to a distal most position, needle capture disc 130 is positioned in the distal end of barrel 102 and adjacent needle guides 124.

Needle capture disc 130 includes needle capture features 132 for receiving and capturing proximal ends 120 of needles 112 so that needles 112 may be drawn proximally out through the percutaneous penetration as needle receiver 126 is pulled via handle 128. As discussed below, pulling handle 128 proximally causes needles 126 to disengage from needle carrier 114 and pull needles 112 through the vessel wall surrounding the puncture site and into barrel 102.

Needle capture features 132 may take any suitable form so long as they can receive and capture (e.g., engage and/or hold) needles 112 so that needles 112 can be drawn up through the vessel wall and through barrel 102. For instance, needle capture features 132 may simply be apertures formed in needle capture disc 130 that are sized to receive and frictionally engage needles 112. In addition, or as an alternative, needles 112 may include barbs that can pass up through the apertures of needle capture features 132 and engage a proximal wall of needle capture disc 130. In other embodiments, needle 112 may include ridges or grooves that can securely engage needle capture features 132 on needle capture disc 130.

With continued reference to FIGS. 1 and 2, specific reference is now made to FIGS. 3-8, which illustrate one exemplary manner of applying and tying a suture loop in a blood vessel wall using device 100. Beginning with FIG. 3, introducer sheath S has been inserted into a tissue tract in the tissue T so that the distal end of introducer sheath S is positioned adjacent to and across puncture site PS. Introducer sheath S may have been previously placed in connection with a conventional intravascular diagnostic or treatment protocol, such as angiography, angioplasty, atherectomy, laser ablation, cardiac mapping, cardiac ablation, or the like.

With introducer sheath S in place, device 100 is introduced through introducer sheath S. As mentioned above, device 100 is introduced with needles 112 disposed in the first or introduction position (e.g., with proximal ends 120 positioned within apertures 113) so that they will fit within the internal diameter of introducer sheath S and through puncture site PS without undesired engagement therebetween. A particular advantage of device 100 is that it can be introduced over guidewire GW which has been used for performing the previous procedures. Thus, should it be necessary for any reason, guidewire GW will remain in place until the very end of the suturing procedure.

Once device 100 is introduced through introducer sheath S and positioned as desired (e.g., with the distal end of barrel 102 adjacent the proximal side of the vessel wall VW, and with needle carrier 114 and needles 112 inserted at least partially into the vessel through puncture site PS), needles 112 are moved or expanded to the second or deployment position or orientation, as shown in FIG. 3. That is, needle carrier 114 is moved distally, which moves needles 112 distally, thereby removing proximal ends 120 from apertures 113. As discussed above, removing proximal ends 120 from apertures 113 allow needles 112 to be moved or reoriented so that proximal ends 120 point toward the vessel walls VW adjacent puncture site PS, as shown in FIG. 3.

Figure 4:
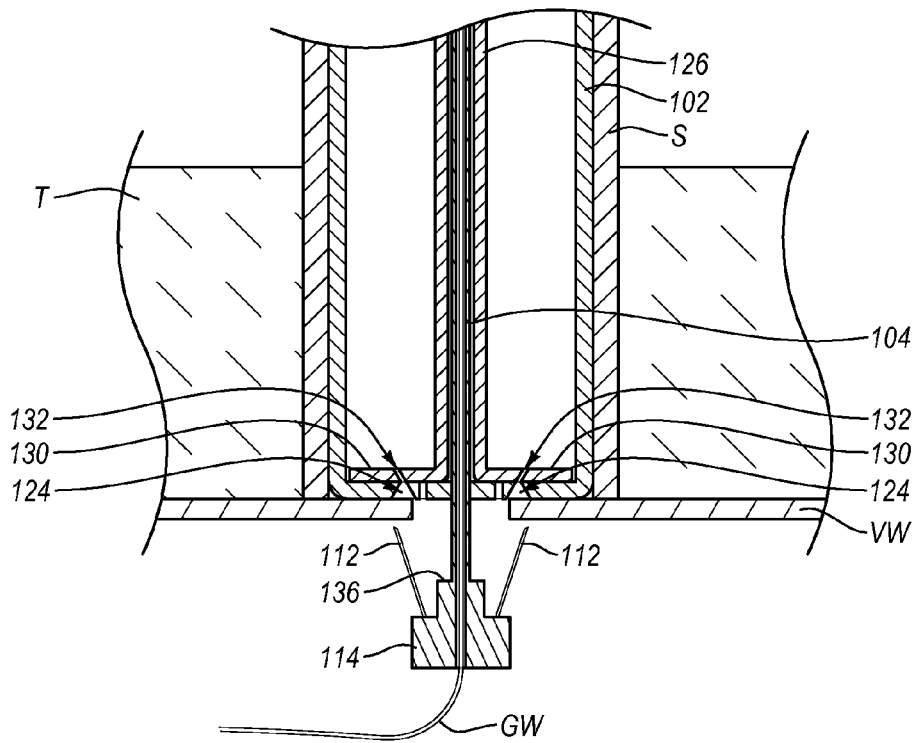
FIG. 4 is a view similar to FIG. 3, except that a needle receiver has been moved distally within the barrel.

With needles 112 expanded to the deployment position, needle receiver 126 is moved distally via handle 128 until needle capture disc 130 is positioned adjacent the distal end of barrel 102, as shown in FIG. 4. When needle capture disc 130 is positioned adjacent the distal end of barrel 102, needle capture features 132 are aligned with needle guides 124

While the present exemplary method has been described with needles 112 being expanded before distal movement of needle receiver 126, it will be understood that needle receiver 126 may be moved distally prior to the expansion of needles 112. That is, once device 100 is introduced through introducer sheath S and positioned as desired (e.g., with the distal end of barrel 102 adjacent the proximal side of the vessel wall VW, and with needle carrier 114 and needles 112 inserted at least partially into the vessel through puncture site PS), needle receiver 126 may be moved to the distal end of barrel 102 and then needles 112 may be expanded as discussed herein.

Figure 5:
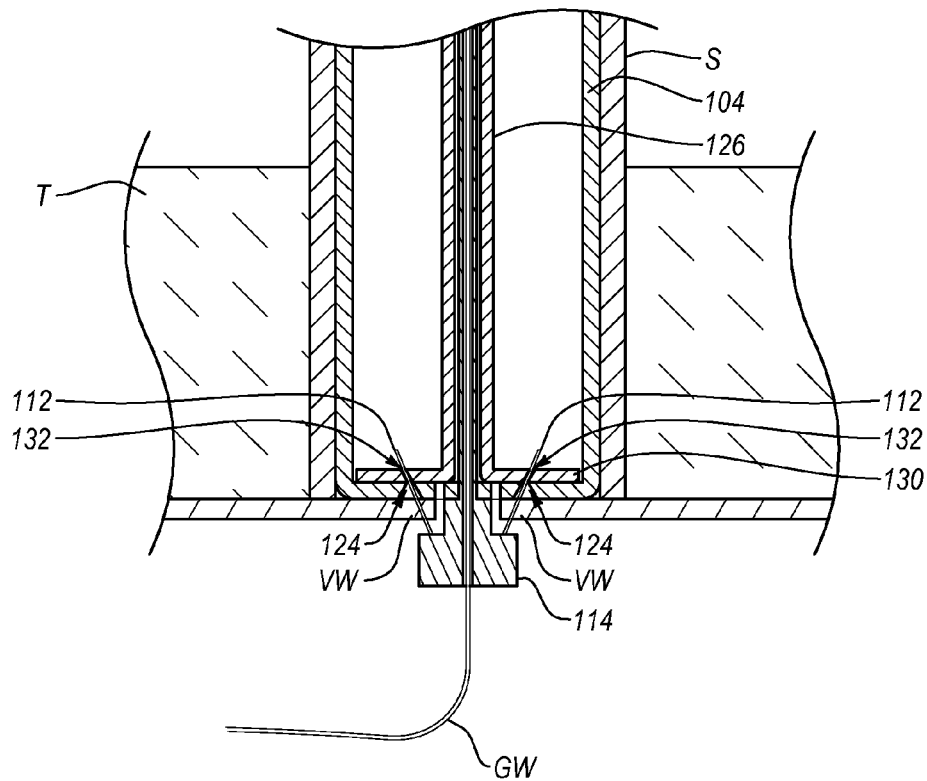
FIG. 5 is a view similar to FIG. 4, except that except that the needles have been drawn back through the vessel wall, through the barrel, and into engagement with the needle receiver.

Regardless of the order in which needles 112 are expanded and needle receiver 126 is moved distally, once both are accomplished, shaft 104 is pulled proximally via handle 124 (see FIGS. 1 and 2), which pulls needle carrier 114 proximally. Shaft 104 is moved proximally until stop member 136, which is disposed on the proximal side of needle carrier 114, engages the distal end of barrel 102, as shown in FIG. 5.

The proximal movement of needle carrier 114 causes expanded needles 112 to penetrate through vessel wall VW. As needles 112 penetrate through opposing sides of vessel wall VW and continue to move proximally, needles 112 pass through needle guides 124 and into or through needle capture features 132, as shown in FIG. 5. As discussed herein, needle guides 124 are configured to direct needles 112 to a desired orientation or location. In particular, needle guides 124 are configured to direct needles 112 into needle capture features 132. As needles 112 pass into or through needle capture features 132, needles 112 and needle capture features 132 are securely engaged with one another, as discussed herein.

Figure 6:
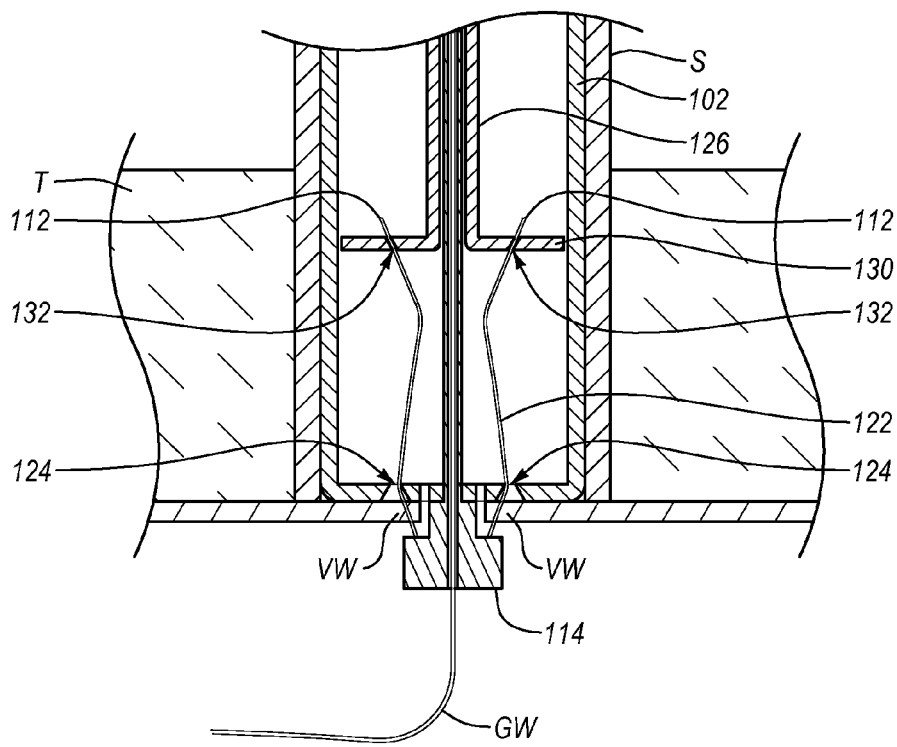
FIG. 6 is a view similar to FIG. 5, except that the needle receiver has been moved proximally to draw the suture through the vessel wall.

With needles 112 held by needle capture features 132, needle receiver 126 is moved proximally via handle 128. Proximal movement of needle receiver 126 when needles 112 are held by needle capture features 132 causes the distal ends of needles 112 to disengage needle carrier 114 and pass through vessel wall VW and needle guides 124, as shown in FIG. 6. As needles 112 continue to move proximally with needle receiver 126, suture 122 passes through the two needle penetrations made in vessel wall VW. The ends of suture 122 that are attached to needles 112 will thus be drawn outward through the percutaneous tract in tissue T, as illustrated in FIG. 6. Sutures 122 may be long enough to permit needle receiver 126 to be pulled adjacent to or completely out of the proximal end of barrel 102 so that needles 112 and the ends of sutures 122 can be accessed outside the tissue tract.

Figure 7:
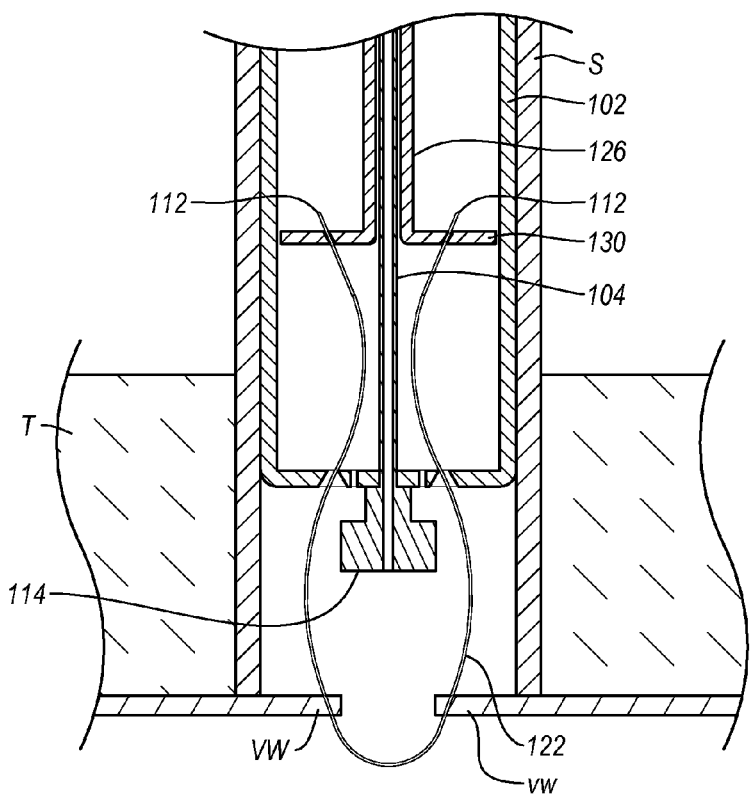
FIG. 7 is a view similar to FIG. 6, except that the suturing device has been moved proximally to remove the needle carrier from the body cavity and further draw the suture through the vessel wall.
Figure 8:
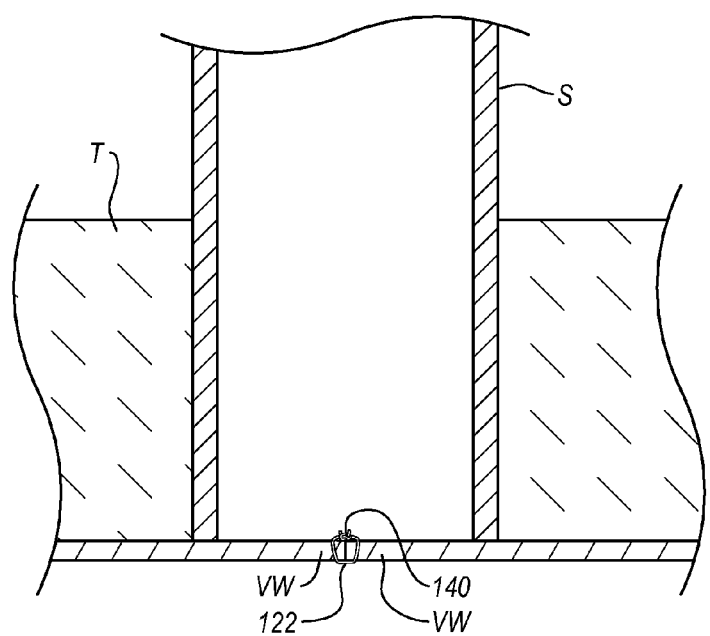
FIG. 8 illustrates the suture tied to close the opening in the vessel wall.

Before pulling suture 122 tight, device 100 is moved proximally via handle 134 or handle 138 to withdraw needle carrier 114 from the vessel, as shown in FIG. 7. Once needle carrier 114 is removed from the vessel, suture 122 can be tightened to close puncture site PS. Suture 122 can be tightened by moving needle receiver 126 proximally by itself, or device 100 as a unit can be moved proximally. In either case, at this point it will be possible to secure the free ends of suture 122 together, e.g., by tying to form a knot 140, as illustrated in FIG. 8. Introducer sheath S may be removed either before or after knot 140 is put in place. As an alternative to tying, various fasteners can be used to secure the free ends of suture 122 together, either alone or in combination with knotting.

As noted above, the needle capturing assembly of the present invention may take various forms. FIGS. 9-11 illustrate an alternate exemplary embodiment of a needle capture system for capturing needles 112 after they have been drawn at least partially through the vessel wall on either side of the puncture site. The needle capture system shown in FIGS. 9-11 is similar in many respect to the needle capture assembly shown in FIGS. 1-7 and can be employed with a suture applying device that is similar to device 100. Thus, in the following description of FIGS. 9-11, elements that are identical to elements from device 100 will be identified with like reference numbers, while similar elements will be identified with reference numbers that are primed (e.g., barrel 102'). Accordingly, the following discussion of FIGS. 9-11 will focus primarily on the features of the illustrated embodiment that are different from those discussed in connection with FIGS. 1-7.

With specific reference to FIG. 9, there is illustrated a partial cross-sectional view of a suture applying device that may be employed to close a puncture site in a vessel wall. In the illustrated embodiment, an introducer sheath S has been inserted into a tract in tissue T so that the distal end of sheath S is positioned across and adjacent to a puncture site PS. As shown in FIG. 9, the suturing applying device has been used to pass a suture 122 through a vessel wall VW on opposing side of puncture site PS. Passing suture 122 through vessel wall VW with the illustrated suture applying device can be accomplished in a manner similar to that described in connection with FIGS. 3-7.

More specifically, with introducer sheath S in place, the suture applying device is introduced through introducer sheath S until needle carrier 114 is positioned at least partially within the vessel and the distal end of barrel 102' is positioned adjacent the proximal side of vessel wall VW. Once the suture applying device is so positioned, needles 112 are moved or expanded from an introduction position or orientation to a deployment position or orientation so that needles 112 are positioned or reoriented to point toward vessel walls VW adjacent puncture site PS. The movement or expansion of needles 112 can be accomplished by moving needle carrier 114 distally to remove the proximal ends of needles 112 from apertures 113', which allows needles 112 to return to their natural position or orientation (e.g., the deployment position with the proximal ends angled away from shaft 104). At this point shaft 104 is pulled proximally, thereby pulling needle carrier 114 and needles 112 proximally so that needles 112 penetrate through vessel wall VW.

When needles 112 penetrate vessel wall VW, needles 112 encounter the distal end of barrel 102'. Unlike the previous embodiment that used needle guides 124 in barrel 102 and a separate needle receiver 126 with needle capture features 132 that captured needles 112, the presently illustrated embodiment consolidates the needle guides and the needle capture features in a needle guide and capture disc 141 that is disposed at the distal end of barrel 102'. As discussed in greater detail below, when needles 112 encounter needle guide and capture disc 141, needles 112 are captured or held by needle guide and capture disc 141. Once needles 112 are captured, barrel 102' is withdrawn proximally, causing needles 112 to disengage needle carrier 114 and pass through vessel wall VW. As needles 112 move proximally with barrel 102', suture 122 passes through the two needle penetrations made in vessel wall VW, as shown in FIG. 9. Needle carrier 114 can then be withdrawn from the vessel and suture 122 can be tightened and secured (e.g., by knotting or securing device) to close puncture site PS.

Consolidating the guide and capture features in a single guide and capture disc reduces the number of discrete steps required to perform the procedure of applying a suture. That is, needles 112 are captured by needle guide and capture disc 141 when needles 112 penetrate vessel wall VW without requiring the user to move a separate needle receiver into place. Likewise, the steps of drawing needles 112 and suture 122 through vessel wall VW and withdrawing barrel 102' are accomplished in a single step rather than first requiring withdrawal of a needle receiver followed by removal of the barrel.

FIGS. 10 and 11 illustrate a plan view and a perspective view of needle guide and capture disc 141. With regard to FIG. 11, the side walls of barrel 102' have been removed for the ease of illustration. Accordingly, the top surface of needle guide and capture disc 141 shown in FIG. 11 is typically on the inside of barrel 102'.

As shown in FIGS. 10 and 11, needle guide and capture disc 141 includes four tabs 142 disposed around an aperture A. Four tabs 142, as illustrated, may be used when four needles 112 and two sutures are used to close a puncture site. In other embodiments, needle guide and capture disc 141 may include two, six, eight, or another number of tabs. As discussed below, each of tabs 142 is designed to receive and capture a needle 112 after the needle has penetrated vessel wall VW. Needle guide and capture disc 141 also includes aperture A, which is adapted to have guidewire GW and shaft 104 extend therethrough.

Each tab 142 is cut on three sides from needle guide and capture disc 141 and includes a fourth side 144 that is attached to needle guide and capture disc 141. The fourth side 144 of each tab 142 may be attached to needle guide and capture disc 141 via a living hinge that allows tab 142 to bend or flex relative to needle guide and capture disc 141.

Each of tabs 142 also includes a fold 146 that extends generally perpendicularly from about fourth side 144 to an opposing side of tab 142. In other embodiments, fold 146 extends between opposing sides of tab 142 and generally parallel to fourth side 144. In any case, fold 146 is designed to give tab 142 a generally inverted V-shape, as indicated by reference number 124'. Similar to the funneling function performed by needle guides 124 discussed above, the inverted V-shape 124' created by fold 146 provides a funneling or guiding effect. As a result of the generally inverted V-shape 124' of tabs 142, tabs 142 can be considered to be generally funnel shaped. More specifically, when needles 112 penetrate vessel wall VW, the inverted V-shape 124' of tab 142 funnels or guides needles 112 into needle capture features 132'. In other words, if needles 112 are deflected, such as by calcified plaque, as they penetrate vessel wall VW, the inverted V-shape 124' of tab 142 will redirect needles 112 toward needle capture features 132'. Thus, tabs 142 can be considered needle guides since they guide the needles toward the needle capture features.

Needle capture features 132' are formed in tabs 142 rather than on a separate needle receiver as described above in connection with FIGS. 1-7. As alluded to, needle capture features 132' are designed to receive and capture the proximal ends of needles 112 so that needles 112 may be drawn proximally out through the percutaneous penetration as barrel 102' is pulled proximally.

Like needle capture features 132, needle capture features 132' may take any suitable form so long as they can receive and capture (e.g., engage and/or hold) needles 112 so that needles 112 can be drawn up through the vessel wall and through barrel 102'. For instance, needle capture features 132' may simply be apertures formed through the apex of the generally inverted V-shape of tabs 142 and which are sized to receive and frictionally engage needles 112. In addition, or as an alternative, needles 112 may include barbs that can pass up through the apertures of needle capture features 132' and engage a proximal wall of tabs 142. In other embodiments, needles 112 may include ridges or grooves that securely engage needle capture features 132'. Once needles 112 are captured by needle capture features 132', barrel 102' can be moved proximally to disengage the distal ends of needles 112 from needle carrier 114 and draw needles 112 and suture 122 up through vessel wall VW so that suture 122 can be secured to close puncture site PS, as discussed above.

Similar to needle guides 124 and apertures 113 referred to above, apertures 113' and tabs 142 may be aligned with one another as shown in FIGS. 9-11. Alternatively, apertures 113' and tabs 142 may be angularly offset from one another about aperture A. Thus, once needles 112 are removed from apertures 113', shaft 104 may be rotated to align needles 112 with tabs 142 (and more specifically needle capture features 132'). Furthermore, apertures 113' may be formed in tabs 142 as shown, or apertures 113' may be formed in another portion of needle guide and capture disc 141, such as between aperture A and tabs 142, for example.

As noted above, the needle capture system of FIGS. 9-11 consolidates the needle guides and the needle capture features in the distal end of the barrel 102'. In an alternative embodiment, however, the needle guides and needle capture features may be consolidated on a needle receiver similar to needle receiver 126 discussed above. More specifically, a plunger-type needle receiver may include a needle guide and capture disc, similar to needle guide and capture disc 141, which can be movably mounted on the shaft. The distal end of the barrel may include one or more openings for receiving the needles therethrough as the needles are drawn proximally through the vessel wall. Once the needles have penetrated the vessel wall and extend into the barrel, the plunger-type needle receiver may be moved distally so that the needle guide and capture disc receives and captures the needles. More particularly, as the plunger-type needle receiver is moved distally, the needles will encounter generally inverted V-shaped tabs that guide the needles to needle capture features in a manner similar to that discussed above. Continued distal movement of the plunger-type needle receiver will cause the needles to be received and captured by the needle capture features. Once the needles have been captured, the plunger-type needle receiver is drawn proximally to drawn the needles up through the barrel, thereby drawing the suture through the vessel wall.

In light of the disclosure herein, it will be understood that the needle guides and needle capture features may be disposed on different elements of a suturing device (e.g., one on a needle receiver and the other on a barrel), may move relative to one another, or may be formed in the same element (e.g., both formed in a barrel or both in a needle receiver), or may remain stationary relative to one another.

Figure 12:
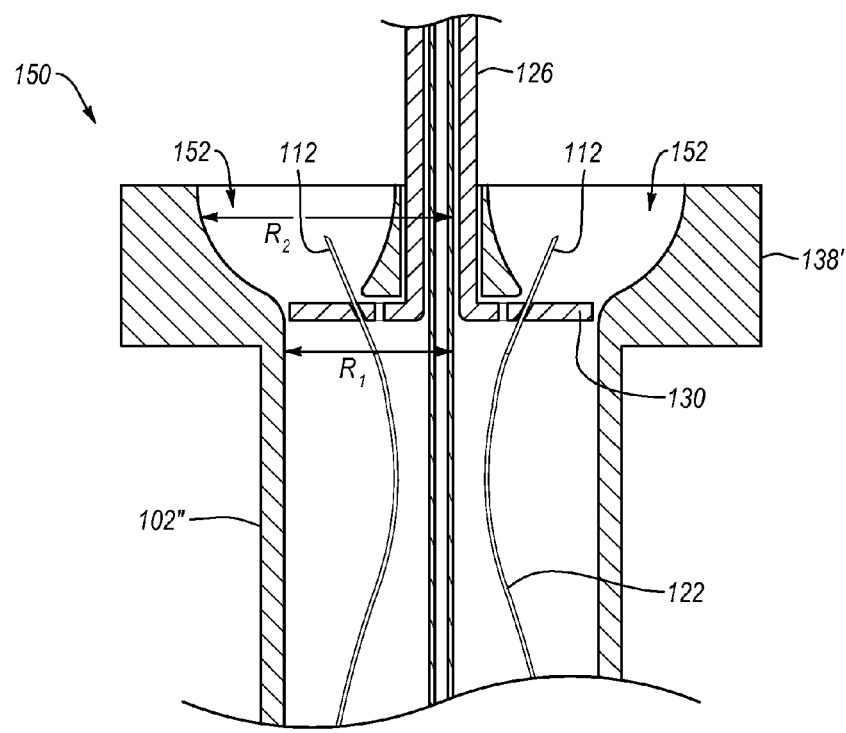
FIG. 12 illustrates a partial cross-sectional view of an exemplary embodiment of a proximal end of a suturing device similar to the suturing device of FIG. 1, with the barrel having cutouts to facilitate retrieval of the needles from the suturing device.

Attention is now directed to FIG. 12, which illustrates a partial cross sectional view of a suture applying device 150 that is similar in many respects to device 100. Specifically, device 150 includes a barrel 102", a shaft 104, and a needle receiver 126 that cooperate to capture and draw needles 112 and suture 122 through a vessel wall so that suture 122 can close a puncture site in the vessel wall. In the illustrated embodiment, shaft 104 and needle receiver 126 are identical to the similarly identified elements of device 100.

As discussed above, once needles 112 have been captured and drawn through the vessel wall, needles 112 are drawn proximally until they can be accessed by a user, at which point they are removed from the suture applying device so that the suture can be tied off. Nevertheless, many suture applying devices are relatively compact, making is difficult for a user to retrieve the needles even after the needles have been fully withdrawn.

In order to facilitate the retrieval of the needles from suture applying device 150, barrel 102" includes cutouts 152 in the proximal end thereof. As shown in FIG. 12, cutouts 152 are disposed adjacent an opening in the proximal end of barrel 102". Cut outs 152 effectively increase the radius of the opening in the proximal end of barrel 102". For instance, barrel 102" may have a generally uniform radius $R_1$ throughout most of its length. Without cutouts 152, the radius of the opening in the proximal end of barrel 102" would also be $R_1$. However, the areas of the opening in barrel 102" that include cutouts 152 have a radius $R_2$ that is larger than radius $R_1$. The increased radius resulting from cutouts 152 gives a user more room, and therefore makes it easier to reach into the opening in barrel 102" and retrieve needles 102.

Attention is now directed to FIGS. 13A-14B, which illustrate alternative exemplary manners and mechanisms for moving needles between introduction and deployment positions or orientations. The embodiments illustrated in these Figures are similar in many respects to the embodiments previously described. Thus, in the following description of FIGS. 13A-14B, elements that are identical to elements from the previous embodiments will be identified with like reference numbers, while similar elements will be identified with reference numbers that are primed (e.g., needle carrier 114').

Figure 13A:
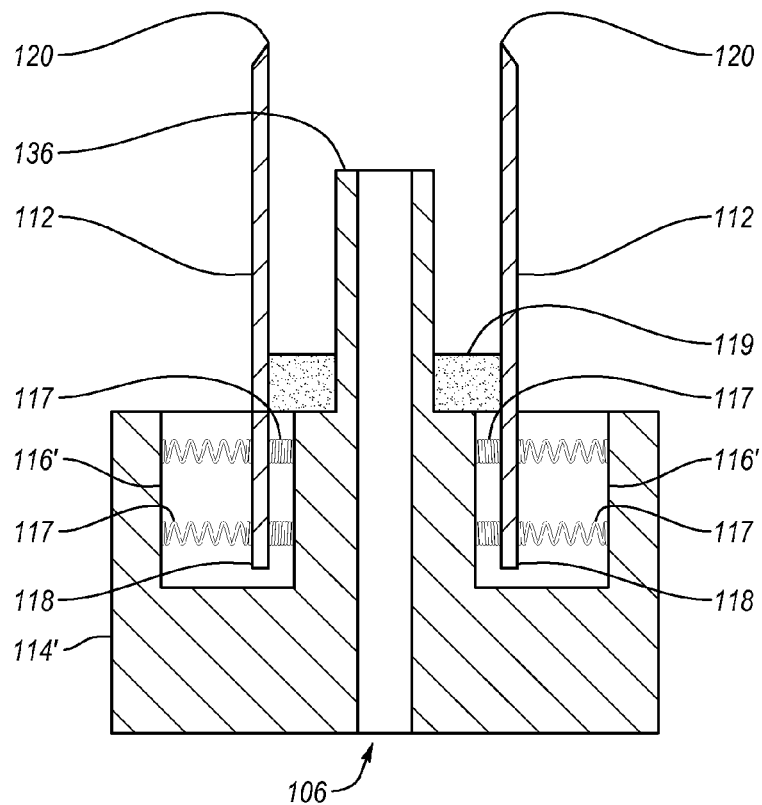
FIG. 13A is a cross-sectional view of a needle carrier according to an exemplary embodiment of the present invention, shown with needles retracted in an introduction position.
Figure 13B:
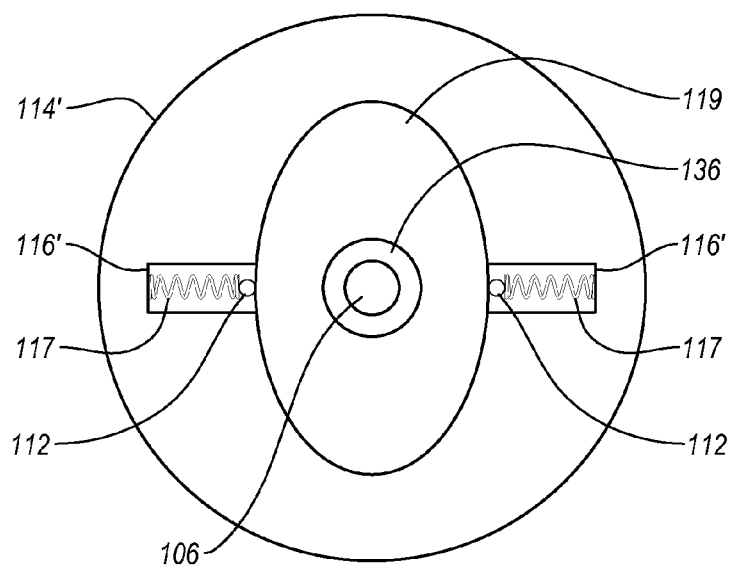
FIG. 13B is a top view of the needle carrier of FIG. 13A, showing a cam mechanism for moving the needles from the introduction position to deployment position.

With attention to FIGS. 13A-13D, there is illustrated a needle carrier 114' which may be mounted at the distal end of shaft 104 (FIG. 1). Needle carrier 114' includes needle receptacles 116' that receive the distal shank portion 118 of needles 112. Needle receptacles 116' are designed to hold needles 112 in a first, introduction position, as shown in FIGS. 13A-13B, while needle carrier 114' is introduced into a patient. In the first, introduction position, needles 112 are oriented generally parallel to guidewire lumen 106, which may be parallel or coaxial with shaft 104. Also, when in the first, introduction position, needles 112 are positioned a first distance away from the center of needle carrier 114'. When in the introduction position, needles 112 may be passed through a puncture site without undesirably engaging the vessel wall.

Figure 13C:
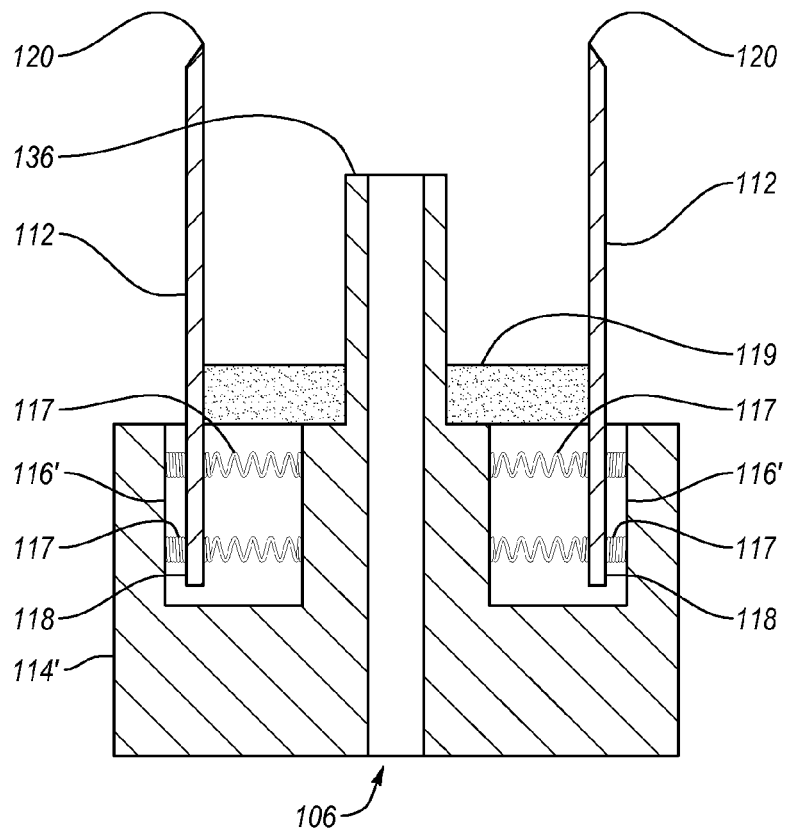
FIG. 13C is a cross-sectional view of the needle carrier of FIG. 13A, shown with the needles in the deployment position.
Figure 13D:
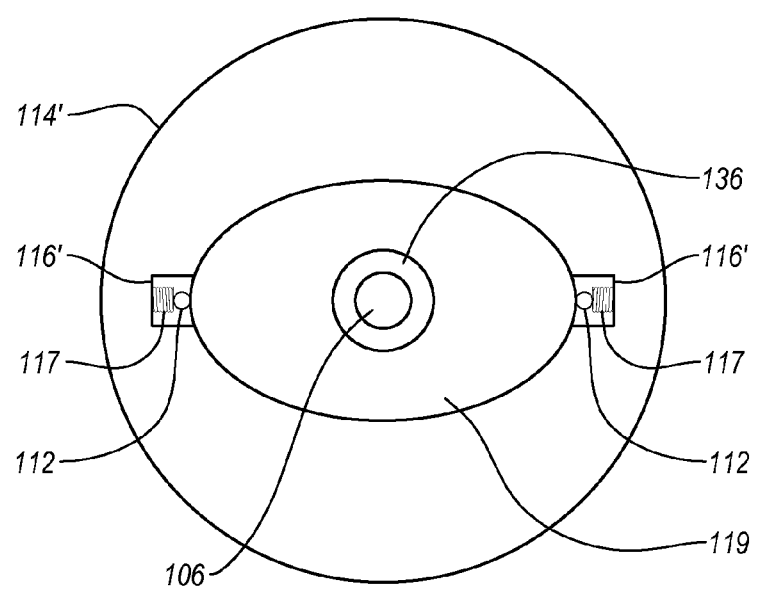
FIG. 13D is a top perspective view of the needle carrier of FIG. 13A, shown with the cam mechanism rotated to move the needles to the deployment position.

Needle receptacles 116' are also designed to hold needles 112 in a second, deployment position, as shown in FIGS. 13C-13D. In the second, deployment position, needles 112 are still oriented generally parallel to guidewire lumen 106. However, when in the second, deployment position, needles 112 are positioned at a second distance that is radially further away from the center of needle carrier 114' than the first position. When in the deployment position, needles 112 may be directed through the vessel wall and received in needles guides 124, as discussed herein.

Needle receptacles 116' are designed to allows needles 112 to selectively move between the first, introduction position and the second, deployment position (e.g., radially closer to and further away from the center of needle carrier 114'). In the presently illustrated embodiment, for example, needle receptacles 116' are configured as slots that allow needles 112 to move therethrough between the first and second distances.

Optionally disposed within or adjacent to needle receptacles 116' are guides 117. Guides 117 may assist with moving needles between the introduction and deployment positions. For instance, guides 117 may include one or more springs or guide rods that help maintain needles 112 in a desired orientation as needles 112 move. Guides 117 may also bias needles 112 toward the introduction position. For instance, when guides 117 include springs, foam, or other biasing material of mechanism, guides 117 may push needles 112 toward the introduction position until another force is applied to overcome the biasing force. Biasing needles 112 in this manner may maintain needles 112 in the introduction position while needle carrier 114' is introduced into a patient.

Once needle carrier 114' is introduced into a patient, in a manner similar to that described elsewhere herein, needles 112 may be selectively moved to the deployment position so that needles 112 may be directed through a vessel wall. To facilitate the movement of needles 112, a cam 119 is positioned on needle carrier 114'. In the illustrated embodiment, cam 19 is generally oval or elliptical in shape and is adapted to rotate generally about the center of needle carrier 114'. For instance, cam 119 may be rotatably disposed about stop member 136. Cam 119 may be connected to an actuator handle disposed at proximal end 108 to enable the selective rotation of cam 119.

When cam 119 is rotated to the position shown in FIGS. 13A-13B (e.g., so the short axis of cam 119 extends between needles 112), needles 112 may be positioned in the introduction position. In contrast, when cam 119 is rotated to the position shown in FIGS. 13C-13D (e.g., so the long axis of cam 119 extends between needles 112), needles 112 are moved to the deployment position. That is, as cam 119 is rotated from the position shown in FIGS. 13A-13B to the position shown in FIGS. 13C-13D, cam 119 pushes needles 112 from the introduction position to the deployment position. The rotation of cam 119 may also overcome any bias force applied by guides 117.

Figure 14A:
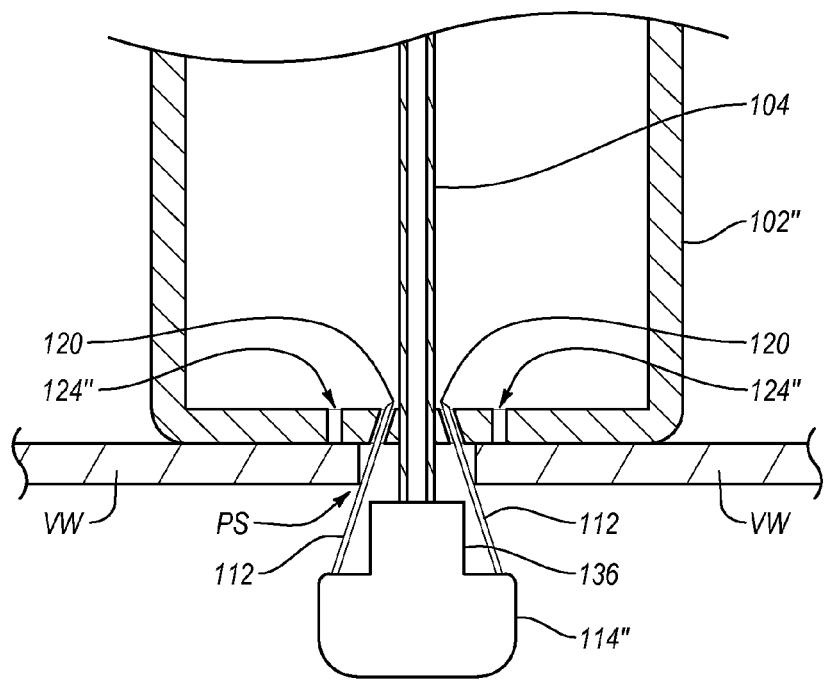
FIG. 14A is a partial cross-sectional view of the distal end of a suturing device according to an exemplary embodiment of the present invention, shown with the needles in an introduction position.
Figure 14B:
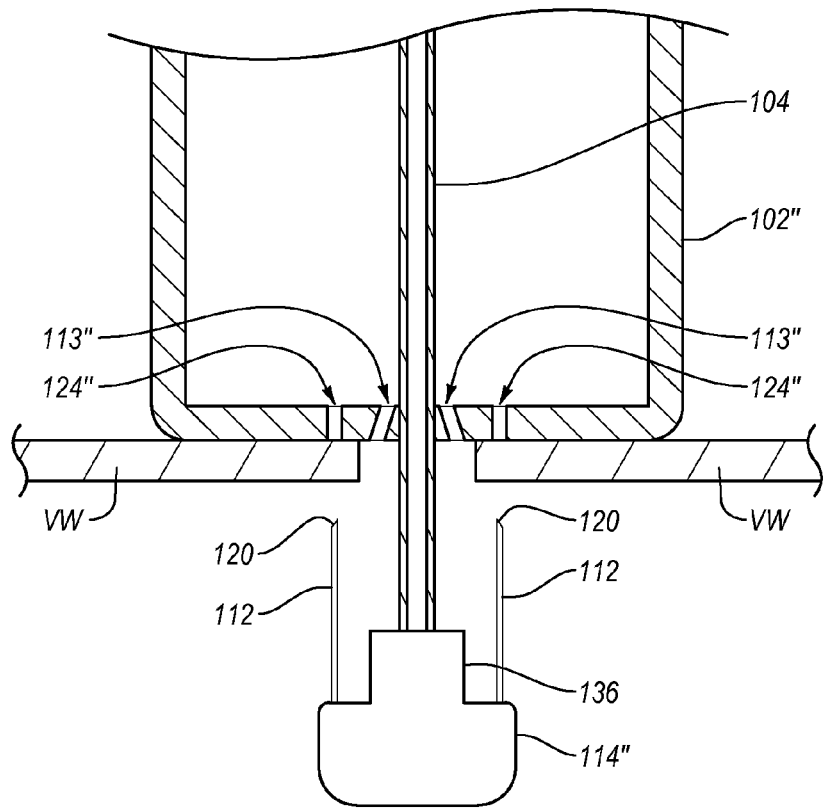
FIG. 14B is a partial cross-sectional view of the distal end of the suturing device of FIG. 14A, shown with the needles in a deployment position.

Attention is now directed to FIGS. 14A-14B, which illustrate another exemplary needle carrier 114". As with the other needle carriers described herein, needle carrier 114" is designed to hold needles 112 in a first, introduction position or orientation (FIG. 14A) and in a second, deployment position or orientation (FIG. 14B). Like the previous embodiments, needles 112 may be held in the first, introduction position to facilitate passage of needles 112 through a puncture site without undesirably engaging the vessel wall. When in the second, deployment position, needles 112 may be directed through the vessel wall and received in needles guides 124", as discussed herein.

According to previous embodiments, needles 112 move between introduction positions that are generally parallel to one of two types of deployment positions. In the first type of deployment position, needles 112 are angled so that proximal ends 120 (i.e., sharpened tips) are disposed radially further away from shaft 104 or the center of the needle carrier than distal shank portions 118 of needles 112. In the second type of deployment position, needles 112 remain generally parallel, but are moved radially away from the center of the needle carrier.

According to the embodiment illustrated in FIGS. 14A-14B, needles 112 are angled so that proximal ends 120 (i.e., sharpened tips) are disposed radially closer to shaft 104 or the center of needle carrier 114" than distal shank portions 118 of needles 11 when needles 112 are in the first, introduction position. In the second, deployment position needles 112 are illustrated as being generally parallel.

As can be seen in FIGS. 14A-14B, needle carrier 114" is wider than puncture site PS. As a result, when needle carrier 114" is passed through puncture site PS and needles 112 are moved to the deployment position, needles 112 will be directed toward the vessel wall VW without having to extend outside the footprint of needle carrier 114". Needles 112 may be moved between the introduction and deployment positions in any suitable manner, including those discussed herein (e.g., with a cam, an effector, being biased to one position and selectively flexed to the other, and the like). Additionally, as shown needle carrier 114" may be formed with rounded corners or with materials or coatings that allow for atraumatic passage of needle carrier 114" through puncture site PS even when needle carrier 114" is wider than puncture site PS.

In light of the disclosure herein, it will be appreciated that the various features of the disclosed embodiments may be included or interchanged with the features of other embodiments. For instance, a needle carrier may be configured to hold needles in an introduction position that is i) generally parallel to shaft 104, ii) angled relative to shaft 104 so that the proximal ends of the needles are radially closer to shaft 104 than the distal ends of the needles, or iii) angled relative to shaft 104 so that the proximal ends of the needles are radially further away from shaft 104 than the distal ends of the needles. Similarly, a needle carrier may be configured to hold needles in a deployment position that is i) generally parallel to shaft 104, ii) angled relative to shaft 104 so that the proximal ends of the needles are radially closer to shaft 104 than the distal ends of the needles, or iii) angled relative to shaft 104 so that the proximal ends of the needles are radially further away from shaft 104 than the distal ends of the needles. Furthermore, needle carriers may be configured to hold needles in any combination of introduction and deployment positions.

Although the embodiments shown and described herein have included needle carriers that hold needles in introduction and deployment positions that are different from one another (by position, orientation, or both), the present invention is not so limited. Rather, a needle carrier according to some embodiments of the present invention may hold needles in a single position or orientation while the needles are introduced into the patient and while the needles are withdrawn through a vessel wall.

With reference to FIG. 14B, for example, a needle carrier 114" may be configured to hold needles 112 in a generally parallel orientation and at a predetermined distance from the center of needle carrier 114". Needle carrier 114" may hold needles 112 in this position and orientation while needle carrier 114" is introduced into a patient through puncture site PS. As needles 112 are being passed through puncture site PS, the vessel wall VW may stretch to slightly increase the size of puncture site PS so that needles 112 may pass therethrough. Alternatively, needles 112 may be configured to flex toward shaft 104 as needles 112 pass through puncture site PS. In any case, once needles 112 have passed through puncture site PS, needles 112 will remain or will return to the original generally parallel orientation, as shown in FIG. 14B. As seen in FIG. 14B, needles 112 are spaced far enough apart that proximal movement of needles 112 will cause needles to penetrate vessel wall VW and be received within needle guides 124", as discussed herein.

Thus, needle carriers according to the present invention may hold needles in various introduction positions/orientations that facilitate the introduction of the needles into a body lumen through a puncture site. The needles carriers may likewise hold needles in various deployment positions/orientations that facilitate the penetration of the needles through a vessel wall surrounding a puncture site. Needles carriers may also hold needles in a single position/orientation that allows for the needles to both pass through a puncture site as well as be withdrawn through a vessel wall.

Even though the suture applying devices are illustrated herein with regard to vascular tissue, it should be understood that the present invention is not limited to any particular type of tissue. Generally, the devices of the present invention can be used for suturing all types of tissue in many applications. More specifically, the present invention can close apertures in tissue or bind layers of tissue together such as in anastomoses.

In one aspect of the disclosure, a suturing device includes a shaft, a pair of needles, a length of suture, a needle receiver, and a barrel.

In another aspect that may be combined with any of the aspects herein, the shaft has a proximal end and a distal end.

In another aspect that may be combined with any of the aspects herein, the pair of needles are removably carried near the distal end of the shaft.

In another aspect that may be combined with any of the aspects herein, each needle includes a first end and a second end having a sharpened tip.

In another aspect that may be combined with any of the aspects herein, the needles are carried with the sharpened tips disposed toward the proximal end of the shaft.

In another aspect that may be combined with any of the aspects herein, the needles are selectively movable between a first position that is generally parallel to the shaft and a second position that is angled relative to the shaft.

In another aspect that may be combined with any of the aspects herein, the length of suture is secured to and extends between the needles.

In another aspect that may be combined with any of the aspects herein, the needle receiver includes a pair of needle capture features which receive and securely hold the needles after the shaft has been drawn proximally.

In another aspect that may be combined with any of the aspects herein, the barrel has a proximal end and a distal end.

In another aspect that may be combined with any of the aspects herein, the barrel is mounted on the shaft such that the shaft can slide relative to the barrel.

In another aspect that may be combined with any of the aspects herein, the distal end of the barrel includes an aperture through which the shaft can extend In another aspect that may be combined with any of the aspects herein, the distal end of the barrel includes a pair of needle guides disposed on opposing sides of the aperture.

In another aspect that may be combined with any of the aspects herein, the needle guides are adapted to guide the needles into the needle capture features.

In another aspect that may be combined with any of the aspects herein, the suturing device further includes a needle carrier disposed on the distal end of the shaft and which removably carries the needles.

In another aspect that may be combined with any of the aspects herein, the needle carrier includes a stop member that engages the distal end of the barrel when the shaft has been drawn proximally.

In another aspect that may be combined with any of the aspects herein, the needle guides are generally funnel-shaped apertures formed through the distal end of the barrel.

In another aspect that may be combined with any of the aspects herein, the needle receiver is slidably mounted on the shaft at least partially within the barrel.

In another aspect that may be combined with any of the aspects herein, the needle receiver slides distally along the shaft to engage the needle capture features with the needles after the needles have been drawn proximally through the needle guides.

In another aspect that may be combined with any of the aspects herein, the needle receiver includes a needle capture disc that extends radially away from the shaft.

In another aspect that may be combined with any of the aspects herein, the needle capture features include apertures formed in the needle capture disc, the apertures being adapted to receive and retain the needles therein.

In another aspect that may be combined with any of the aspects herein, the distal end of the barrel include a pair of tabs.

In another aspect that may be combined with any of the aspects herein, the pair of tabs includes the needle capture features and the needle guides.

In another aspect that may be combined with any of the aspects herein, each tab has a generally inverted V-shape that forms the needle guide.

In another aspect that may be combined with any of the aspects herein, the generally inverted V-shaped tabs guide the needles to the needle capture features as the shaft is drawn proximally.

In another aspect that may be combined with any of the aspects herein, the barrel has a proximal end and a distal end and is slidably mounted on the shaft to facilitate relative movement therebetween.

In another aspect that may be combined with any of the aspects herein, the distal end of the barrel includes a pair of needle guides that guide the needles into the barrel in a predetermined orientation as the shaft is drawn proximally relative to the barrel.

In another aspect that may be combined with any of the aspects herein, the needle receiver is slidably mounted on the shaft and at least partially within the barrel.

In another aspect that may be combined with any of the aspects herein, the needle receiver is movable relative to the shaft and the barrel.

In another aspect that may be combined with any of the aspects herein, the needle receiver includes a needle capture disc that extends radially away from the shaft and which includes a pair of needle capture features that receive and securely hold the needles after the shaft has been drawn proximally to draw the needles through the needle guides and upon distal movement of the needle receiver.

In another aspect that may be combined with any of the aspects herein, the needle guides are generally funnel-shaped apertures formed through the distal end of the barrel.

In another aspect that may be combined with any of the aspects herein, the needle capture features include apertures formed in the needle capture disc to receive and retain the needles therein.

In another aspect that may be combined with any of the aspects herein, the distal end of the barrel includes a pair of needle guides and a pair of needle capture features.

In another aspect that may be combined with any of the aspects herein, the needle guides are generally funnel-shaped to guide the needles toward the needle capture features as the shaft is drawn proximally relative to the barrel.

In another aspect that may be combined with any of the aspects herein, the distal end of the barrel includes a pair of tabs, each tab including a needle capture feature and a needle guide.

In another aspect that may be combined with any of the aspects herein, each tab has a generally inverted V-shape that forms the needle guide for guiding the needles to the needle capture features as the shaft is drawn proximally.

In another aspect that may be combined with any of the aspects herein, the needle capture features includes apertures formed in the tabs generally at an apex of the generally inverted V-shape, the needle capture feature apertures being adapted to receive and securely hold the needles therein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suturing device comprising:
a shaft having a proximal end and a distal end
a pair of needles removably carried near the distal end of the shaft, each needle including a first end and a second end having a sharpened tip, the needles being carried with the sharpened tips disposed toward the proximal end of the shaft;
a length of suture secured to and extending between the needles;
a needle receiver comprising a lumen that receives the shaft in sliding engagement, a distal end, and a pair of needle capture features formed in the distal end which receive and securely hold the needles after the shaft has been drawn proximally relative to the needle receiver, the needle receiver comprising a needle capture disc that extends radially away from the shaft and includes the pair of needle capture features;
a barrel having a proximal end and a distal end, the barrel being mounted on the shaft such that the shaft can slide relative to the barrel, the distal end of the barrel comprising an aperture through which the shaft can extend and a pair of needle guides that are radially offset from one another, the needle guides being adapted to guide the needles into the needle capture features in a desired orientation.

2. The suturing device of claim 1, further comprising a needle carrier disposed on the distal end of the shaft, the needle carrier removably carrying the needles.

3. The suturing device of claim 2, wherein the needle carrier facilitates movement of the needles between a first position and a second position.

4. The suturing device of claim 2, wherein the needle carrier comprises a stop member that engages the distal end of the barrel when the shaft has been drawn proximally.

5. The suturing device of claim 1, wherein the needle guides are generally funnel-shaped apertures formed through the distal end of the barrel.

6. The suturing device of claim 1, wherein the needle receiver is slidably mounted on the shaft at least partially within the barrel.

7. The suturing device of claim 1, wherein the needle receiver slides distally along the shaft to engage the needle capture features with the needles after the needles have been drawn proximally through the needle guides.

8. The suturing device of claim 1, wherein the needle capture features comprise apertures formed in the needle capture disc, the apertures being adapted to receive and retain the needles therein.

9. The suturing device of claim 1, wherein the distal end of the barrel comprises a pair of tabs.

10. The suturing device of claim 9, wherein the pair of tabs comprises the needle capture features and the needle guides.

11. The suturing device of claim 10, wherein each tab has a generally inverted V-shape that forms the needle guide, wherein the generally inverted V-shaped tabs guide the needles to the needle capture features as the shaft is drawn proximally.

12. The suturing device of claim 1, wherein the needles are selectively movable between a first position and a second position.

13. The suturing device of claim 12, wherein the distal end of the barrel comprises a pair of apertures that selectively receive therein the sharpened tips of the pair of needles, wherein the pair of needles are maintained in the first position when the sharpened tips are received within the pair of apertures, and wherein the pair of needles move to the second position when the sharpened tips are removed from the pair of apertures.

14. The suturing device of claim 12, wherein the needles are generally parallel to the shaft when in the first position.

15. The suturing device of claim 12, wherein the needles are angled relative to the shaft when in the second position.

16. The suturing device of claim 12, wherein the needles are angled relative to the shaft when in the first position.

17. The suturing device of claim 12, wherein the needles are generally parallel when in the second position.

18. The suturing device of claim 1, wherein the pair of needle guides are disposed on opposing sides of the aperture.

19. A suturing device comprising:
a shaft having a proximal end and a distal end;
a pair of needles removably carried near the distal end of the shaft, each needle including a shank carried near the distal end of the shaft and a sharpened tip disposed toward the proximal end of the shaft, each needle being selectively movable between a first position that is generally parallel to the shaft and a second position that is angled relative to the shaft;
a length of suture secured to and extending between the needles; and
a barrel having a proximal end and a distal end, the barrel being slidably mounted on the shaft to facilitate relative movement therebetween, the distal end of the barrel comprising an aperture through which the shaft can extend and a pair of needle guides that guide the needles into the barrel in a predetermined orientation as the shaft is drawn proximally relative to the barrel; and
a needle receiver slidably mounted on the shaft and at least partially within the barrel, the needle receiver being movable relative to the shaft and the barrel, the needle receiver comprising a needle capture disc that extends radially away from the shaft, the needle capture disc comprising a pair of needle capture features which receive and securely hold the needles after the shaft has been drawn proximally to draw the needles through the needle guides and upon distal movement of the needle receiver.

20. The suturing device of claim 19, wherein the needle guides are generally funnel-shaped apertures formed through the distal end of the barrel.

21. The suturing device of claim 19, further comprising a needle carrier disposed on the distal end of the shaft, the needle carrier removably carrying the needles.

22. The suturing device of claim 19, wherein the barrel comprises a handle at the proximal end thereof, the handle comprising cutouts to facilitate the retrieval of the needles from the barrel after the needle receiver has been drawn to its extreme proximal position relative to the barrel.

23. The suturing device of claim 19, wherein the needle capture features comprise apertures formed in the needle capture disc, the apertures being adapted to receive and retain the needles therein.

24. The suturing device of claim 19, wherein the pair of needles are biased toward the second position.

* * * * *